US00PP28253P2

(12) United States Plant Patent
Beekenkamp

(10) Patent No.: US PP28,253 P2
(45) Date of Patent: Aug. 8, 2017

(54) POINSETTIA PLANT NAMED 'BKPONAR'

(50) Latin Name: ***Euphorbia pulcherrima* Willd.**
Varietal Denomination: Bkponar

(71) Applicant: Annie Cornelia Beekenkamp, Maasdijk (NL)

(72) Inventor: Annie Cornelia Beekenkamp, Maasdijk (NL)

(73) Assignee: BeekenKamp Plants B.V., Maasdijk (NL)

( * ) Notice: Subject to any disclaimer, the term of this patent is extended or adjusted under 35 U.S.C. 154(b) by 0 days.

(21) Appl. No.: 14/998,879

(22) Filed: Feb. 25, 2016

(51) Int. Cl.
*A01H 5/02* (2006.01)

(52) U.S. Cl.
USPC ..... Plt./307

(58) Field of Classification Search
USPC ..... Plt./307
See application file for complete search history.

*Primary Examiner* — Anne Grunberg
(74) *Attorney, Agent, or Firm* — C. A. Whealy

(57) ABSTRACT

A new and distinct cultivar of Poinsettia plant named 'Bkponar', characterized by its broadly upright and uniformly mounding plant habit; moderately vigorous growth habit; freely branching habit; dark green-colored leaves; large and full inflorescences with bright red-colored flower bracts; and excellent post-production longevity.

2 Drawing Sheets

Botanical designation: *Euphorbia pulcherrima* Willd.
Cultivar denomination: 'BKPONAR'.

BACKGROUND OF THE INVENTION

The present invention relates to a new and distinct cultivar of Poinsettia plant, botanically known as *Euphorbia pulcherrima* Willd. and hereinafter referred to by the name 'Bkponar'.

The new Poinsettia plant is a product of a planned breeding program conducted by the Inventor in De Kwakel, The Netherlands. The objective of the breeding program is to create new uniform and freely-branching Poinsettia plants with good postproduction longevity.

The new Poinsettia plant originated from a cross-pollination made by the Inventor in January, 2009 in De Kwakel, The Netherlands of a proprietary selection of *Euphorbia pulcherrima* Willd. identified as code number 2000417, not patented, as the female, or seed, parent with a proprietary selection of *Euphorbia pulcherrima* Willd. identified as code number 2000430, not patented, as the male, or pollen, parent. The new Poinsettia plant was discovered and selected by the Inventor as a single flowering plant within the progeny of the stated cross-pollination in a controlled greenhouse environment in De Kwakel, The Netherlands in December, 2011.

Asexual reproduction of the new Poinsettia plant by terminal vegetative cuttings in a controlled greenhouse environment in Maasdijk, The Netherlands since March, 2012 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bkponar'. These characteristics in combination distinguish 'Bkponar' as a new and distinct Poinsettia plant:

1. Broadly upright and uniformly mounding plant habit.
2. Moderately vigorous growth habit.
3. Freely branching habit.
4. Dark green-colored leaves.
5. Large and full inflorescences with bright red-colored flower bracts.
6. Excellent post-production longevity.

Plants of the new Poinsettia can be compared to plants of the female parent selection. Plants of the new Poinsettia differ primarily from plants of the female parent selection in the following characteristics:

1. Plants of the new Poinsettia are more upright than and not as broad as plants of the female parent selection.
2. Plants of the new Poinsettia have darker green-colored leaves than plants of the female parent selection.
3. Plants of the new Poinsettia have darker red-colored flower bracts than plants of the female parent selection.

Plants of the new Poinsettia can be compared to plants of the male parent selection. Plants of the new Poinsettia differ primarily from plants of the male parent selection in the following characteristics:

1. Plants of the new Poinsettia are more upright than and not as broad as plants of the male parent selection.
2. Plants of the new Poinsettia have lighter green-colored leaves than plants of the male parent selection.
3. Plants of the new Poinsettia and the male parent selection differ in flower bract color as flower bracts of the male parent selection are pink in color.

Plants of the new Poinsettia can be compared to plants of *Euphorbia pulcherrima* Willd. 'Floasatur', disclosed in U.S. Plant Pat. No. 20,230. In side-by-side comparisons conducted in De Kwakel, The Netherlands, plants of the new Poinsettia differ primarily from plants of 'Floasatur' in the following characteristics:

1. Plants of the new Poinsettia are more freely branching than plants of 'Floasatur'.
2. Plants of the new Poinsettia flower earlier than plants of 'Floasatur'.
3. Flower bracts of plants of the new Poinsettia are more rugose than flower bracts of 'Floasatur'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet comprises a side perspective view of a typical flowering plant of 'Bkponar' grown in a container.

The photograph on the second sheet is a close-up view of a typical flowering plant of 'Bkponar'.

DETAILED BOTANICAL DESCRIPTION

The aforementioned photographs and following observations and measurements describe plants grown during the autumn and winter in 13-cm containers in a glass-covered greenhouse in De Kwakel, The Netherlands and under cultural practices typical of commercial Poinsettia production. During the production of the plants, day temperatures ranged from 17° C. to 18° C. and night temperatures ranged from 15° C. to 16° C. Plants were pinched one time and were 23 weeks old when the photographs and the detailed description were taken. In the following description, color references are made to The Royal Horticultural Society Colour Chart, 2015 Edition, except where general terms of ordinary dictionary significance are used.

Botanical classification: *Euphorbia pulcherrima* Willd. 'Bkponar'.

Parentage:

*Female, or seed, parent*.—Proprietary selection of *Euphorbia pulcherrima* Willd. identified as code number 2000417, not patented.

*Male, or pollen, parent*.—Proprietary seedling selection of *Euphorbia pulcherrima* Willd. identified as code number 2000430, not patented.

Propagation:

*Type*.—Terminal vegetative cuttings.

*Time to initiate roots, summer and winter*.—About 18 days at temperatures about 19° C. to 21° C.

*Time to produce a rooted young plant, summer*.—About three weeks at temperatures about 17° C. to 19° C.

*Time to produce a rooted young plant, winter*.—About four weeks at temperatures about 17° C. to 19° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Broadly upright and uniformly mounded plant habit; inverted triangle with rounded crown; large full inflorescences positioned above the foliar plane; moderately vigorous growth habit and moderate growth rate.

*Plant height, soil level to top of foliar plane*.—About 26.4 cm.

*Plant height, soil level to top of floral plane*.—About 29.9 cm.

*Plant diameter or spread*.—About 47.2 cm.

*Lateral branch description*.—Branching habit: Freely branching habit, about six lateral branches develop after pinching. Length: About 25.7 cm. Diameter: Thick, about 7 mm. Internode length: About 1.6 cm. Strength: Moderately strong. Texture and luster: Smooth, glabrous; glossy. Angle: About 35° from vertical. Color, when developing: Close to 146B. Color, fully developed: Close to 147A.

*Leaf description*.—Arrangement: Alternate, simple. Length: About 11.4 cm. Width: About 9.2 cm. Shape: Ovate. Apex: Apiculate. Base: Obtuse to very short acuminate. Margin: Shallowly lobed, slightly angulate. Venation pattern: Pinnate. Texture and luster, upper and lower surfaces: Slightly rugose, glabrous; matte. Color: Developing leaves, upper surface: Close to 143A. Developing leaves, lower surface: Close to 138A to 138B. Fully expanded leaves, upper surface: Darker than between 147A and N189A; venation, close to between NN137D and N138B. Fully expanded leaves, lower surface: Close to 182A to 183C; venation, close to 182A to 182C. Petioles: Length: About 6.5 cm. Diameter: About 3 mm. Texture and luster, upper and lower surfaces: Glabrous; glossy. Color, upper surface: Close to 187A. Color, lower surface: Close to 183A to 183B.

Inflorescence description:

*Inflorescence type and habit*.—Large full inflorescences are compound corymbs of cyathia with bright red-colored flower bracts subtending the cyathia; one inflorescence per lateral branch with inflorescences positioned above and beyond the foliar plane.

*Fragrance*.—None detected.

*Natural flowering season*.—Plants flower naturally during the winter under long nyctoperiod conditions; inflorescence initiation and development can be induced under artificial long nyctoperiod conditions; early flowering habit, response time is about seven weeks.

*Post-production longevity*.—Excellent post-production longevity; plants of the new Poinsettia maintain good substance and bract color for about 30 days; flower bracts not persistent.

*Flower bracts*.—Quantity per inflorescence: About 17. Length: About 11.8 cm. Width: About 10 cm. Shape: Broadly ovate. Apex: Apiculate. Base: Obtuse to short acuminate. Margin: Entire; slightly to moderately repand. Venation: Pinnate. Texture and luster, upper and lower surfaces: Slightly rugose, glabrous; matte. Aspect: Mostly horizontal to slightly drooping. Color: Developing bracts, upper surface: Slightly darker than 53A. Developing bracts, lower surface: Close to 46A. Fully expanded bracts, upper surface: Close to N45B and 46B; venation, close to N45B; color does not fade with development. Fully expanded bracts, lower surface: Close to N45C and 46C; venation, close to N45C; color does not fade with development. Bract petioles: Length: About 2 cm. Diameter: About 2 mm. Texture and luster, upper and lower surfaces: Glabrous; glossy. Color, upper surface: Close to 187B. Color, lower surface: Close to 187C.

*Cyathia*.—Quantity per corymb: About ten. Length: About 1.3 cm. Width: About 8 mm. Shape: Ovoid. Texture and luster, inner and outer surfaces: Glabrous; matte. Color, developing, inner surface: Close to 146C. Color, developing, outer surface: Close to 143B; towards the apex, close to N45C to N45D. Color, fully developed, inner surface: Close to 144C; towards the apex, close to 47A. Color, fully developed, outer surface: Close to 143B; towards the apex, close to 47A. Nectaries: Quantity per cyathium: Typically two. Length: About 2 mm. Diameter: About 2 mm. Shape: Club-shaped. Texture and luster, inner and outer surfaces: Glabrous; matte. Color, developing and fully developed, inner surface: Close to 144C to 144D. Color, developing and fully developed, outer surface: Close to 144C.

*Peduncles*.—Length: About 3 mm to 6 mm. Diameter: About 2 mm to 3 mm. Strength: Moderately strong. Aspect: Erect to about 45° from vertical. Texture and luster: Glabrous; glossy. Color: Close to 144A.

*Reproductive organs*.—Stamens: Quantity per cyathium: About ten. Filament length: About 5 mm. Filament color: Close to 46A. Anther shape: Club-shaped. Anther length: About 2 mm. Anther color: Close to 46A. Amount of pollen: Moderate. Pollen color: Close to 12A. Pistils: Pistil development has not been observed on plants of the new Poinsettia. Seeds and fruits: Seed and fruit production has not been observed on plants of the new Poinsettia.

Pathogen & pest resistance: Plants of the new Poinsettia have not been shown to be resistant to pathogens and pests common to Poinsettia plants.

Temperature tolerance: Plants of the new Poinsettia have been observed to tolerate high temperature about 35° C. and to be suitable for USDA Hardiness Zones 10 to 12.

It is claimed:

1. A new and distinct Poinsettia plant named 'Bkponar' as illustrated and described.

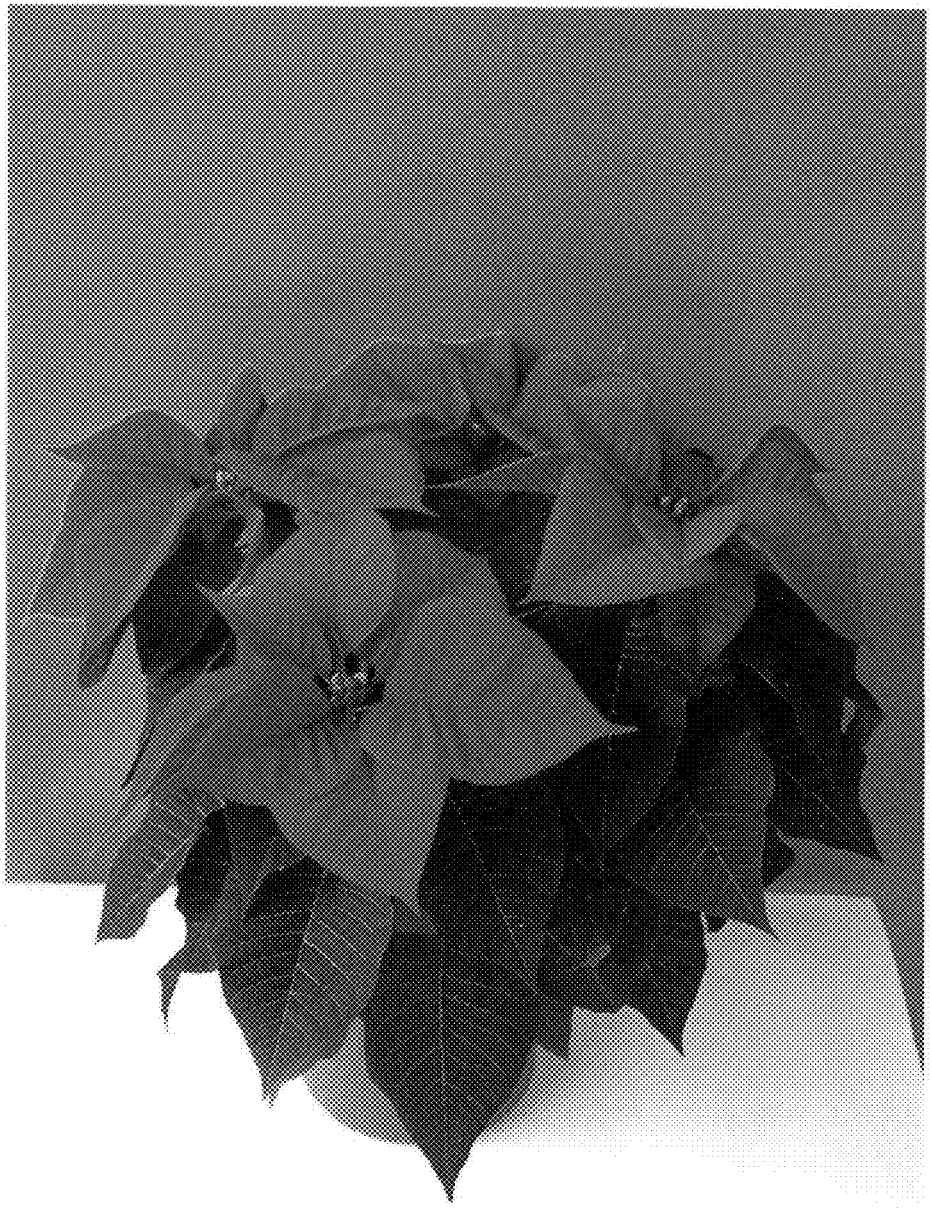

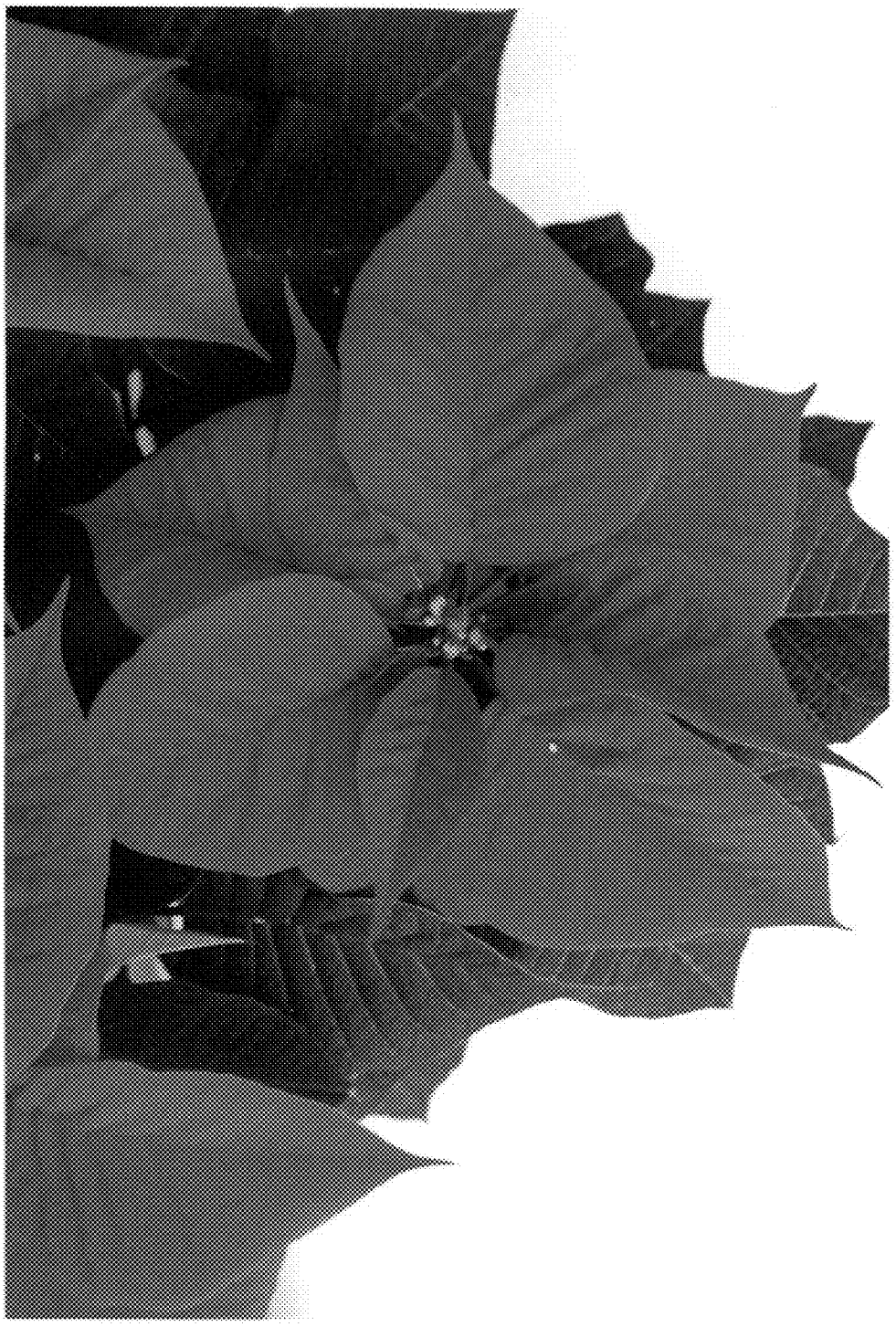

* * * * *